(12) United States Patent
Petschner

(10) Patent No.: US 7,296,710 B2
(45) Date of Patent: Nov. 20, 2007

(54) CONTAINER FOR MEDICAL OPHTHALMIC PREPARATIONS AND PROTECTIVE CAP FOR SUCH A CONTAINER

(76) Inventor: Thomas Petschner, Markstrasse 20, 65183 Wiesbaden (DE)

( * ) Notice: Subject to any disclaimer, the term of this patent is extended or adjusted under 35 U.S.C. 154(b) by 349 days.

(21) Appl. No.: 10/909,510

(22) Filed: Aug. 2, 2004

(65) Prior Publication Data

US 2005/0184089 A1    Aug. 25, 2005

(51) Int. Cl.
*B65D 35/28* (2006.01)

(52) U.S. Cl. ........................ 222/103; 604/289

(58) Field of Classification Search ........... 222/103, 222/95, 333, 420, 421, 460–462, 100, 105, 222/106; 604/289–302
See application file for complete search history.

(56) References Cited

U.S. PATENT DOCUMENTS

| | | | |
|---|---|---|---|
| 2,626,606 A * | 1/1953 | Campbell | 604/301 |
| 2,920,624 A | 1/1960 | Lerner et al. | |
| 3,279,466 A | 10/1966 | Mings | |
| 3,602,217 A * | 8/1971 | Felton et al. | 601/72 |
| 4,758,237 A * | 7/1988 | Sacks | 604/294 |
| 5,893,515 A * | 4/1999 | Hahn et al. | 239/7 |
| 6,758,837 B2 * | 7/2004 | Peclat et al. | 604/295 |

FOREIGN PATENT DOCUMENTS

| | | | | |
|---|---|---|---|---|
| DE | 2817979 | | 7/1984 | |
| DE | 8428556 | | 12/1984 | |
| DE | 9414153 | | 12/1994 | |
| DE | 10147799 | | 4/2003 | |
| FR | 2694492 | * | 8/1992 | 604/301 |
| JP | 10211255 | | 8/1998 | |
| JP | 2000024080 | | 1/2000 | |
| JP | 2001050616 | | 9/2002 | |

* cited by examiner

*Primary Examiner*—Lien M. Ngo
(74) *Attorney, Agent, or Firm*—Greer Burns & Crain, Ltd

(57) ABSTRACT

The container for medical ophthalmic preparations has an exit opening which is formed in an arcuate indentation of the container wall that passes at both sides into a respective arcuate bulge. The container is placed with said wave-like container wall on the area of the eyebrow and cheekbones, the indentation making sure that there is no contact with the surface of the eye. A protective cap for a conventional container for medical ophthalmic preparations has a corresponding wave-like contour. Said contour ensures a safety distance from the eye, which excludes any injuries. The container and the protective cap can be handled easily in the case of a self-administration of the eye drops—even by persons with motoric disorders.

2 Claims, 2 Drawing Sheets

CONTAINER FOR MEDICAL OPHTHALMIC PREPARATIONS AND PROTECTIVE CAP FOR SUCH A CONTAINER

FIELD OF THE INVENTION

The present invention relates to a container for medical ophthalmic preparations. Furthermore, the invention relates to a protective cap for a container for medical ophthalmic preparations.

BACKGROUND OF THE INVENTION

Medical ophthalmic preparations are normally administered dropwise by holding and slightly compressing a small bottle-like container with the liquid preparation with its pointed outlet closely above the wide-opened eye. The exiting drops of the preparation are meant to fall on the eyeball. The self-administration of eye drops requires considerable skill and discipline because looking at the pointed outlet end of the container near the eye automatically causes anxiety and prompts one to close the eye. With old people showing motoric disorders, such as trembling hands, such a self-administration of eye drops entails the risk that the eye gets injured so that persons handicapped in this way, and also infants, depend on the help of another person administering the drops.

OBJECT OF THE INVENTION

It is the object of the present invention to indicate a solution for the above-described problem with which the self-administration of liquid ophthalmic preparations is facilitated and eye injuries during this process are safely avoided.

SUMMARY OF THE INVENTION

According to the invention this object is achieved by a container for medical opthalmic preparations and a protective cap for such a container.

The container of the invention is configured such that its exit opening is formed in an indentation of the container wall, said indentation being reset relative to the surrounding wall portions such that there is no contact of the container wall with the surface of the eye when the container is placed on the area of the eyebrow and the cheekbone. The indentation should here be so deep that eyelashes are not touched either, which might otherwise lead to a reflex-like closing of the eye. Preferably, the indentation has a concave arc shape and passes at both sides into a respective convex arcuate bulge.

A safety distance from the eye is automatically ensured by such a configuration, so that an injury of the eye during application of the drops is excluded. The application is considerably facilitated because the container is not freely held in the hand above the eye, but it is placed on the areas surrounding the eye, so that the correct discharge position of the exit opening above the eye is obtained virtually automatically. Since an eye injury is ruled out with certainty, possible feelings of anxiety are also avoided or at least lessened.

The exit opening of the container may have any desired plug to be opened, for instance a standard screw cap. What is important is that the outlet of the container is reset in the indentation of the container wall relative to the contact portions on eyebrow and cheekbones that surround the indentation, namely to such a degree that any contact with the surface of the eye is excluded.

Preferably, the container has a flat shape so that whenever the container is standing on its base, the upper container wall which includes the indentation and the two bulges has essentially the shape of a strip. In comparison with a container that is e.g. round in cross section, this has the advantage that the eye receiving the drops can clearly see the container opening, so that the container can be positioned easily and exactly. However, it goes without saying that compact container shapes are also within the scope of the invention.

The container may consist of an outer container of a relatively rigid plastic material and a soft inner bag which contains the ophthalmic preparation, the preparation drops being dischargeable by exerting pressure on the outer container.

However, it is also possible that the outer container has disposed therein a small battery-driven electric motor and a pressure generating means for the inner bag that is operated by the electric motor. The inner bag may e.g. be arranged between clamp jaws that are movable towards one another by motor power. In such a configuration of the invention, the inner bag is accommodated in the outer container for replacement.

The pressure generating means may create such a pressure that the eye drops are discharged from the exit opening which is at the top during use, so that the container can rest on a support, such as a table, when the eye drops are administered while the eye is positioned above the exit opening. This enables even people with strong motoric disorders to administer the eye drops to themselves.

Under a further aspect of the present invention a protective cap for a preferably conventional container for medical ophthalmic preparations is provided, said protective cap comprising an exit opening in an indentation of the protective cap wall. Said protective cap is mounted on a conventional container for the administration of preparation drops after its plug, for instance a screw cap, has been removed, the protective cap being here configured such that its exit opening covers or surrounds the outlet of the container. The indentation in the protective cap is again reset relative to the bulges at both sides to such an extent that any contact of the eye with the protective cap and the outlet of the container is made impossible when the protective cap is placed on the area of an eyebrow and a cheekbone. Preferably, the protective cap has also a flat disk-like shape.

Further details of the invention will become apparent from the following description of some preferred embodiments and with reference to the drawings.

DETAILED DESCRIPTION OF PREFERRED EMBODIMENTS

Figure 1:
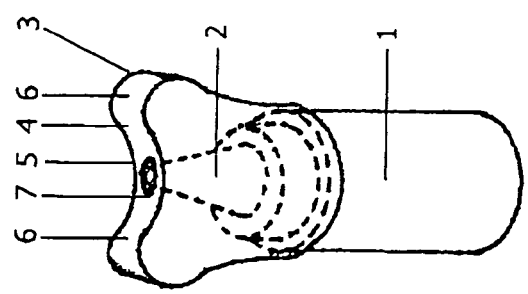
FIG. 1 is a prespective view of a protective cap of the invention placed on a conventional container.

FIG. 1 shows a conventional container 1 for a liquid medical ophthalmic preparation, the container including a substantially conically tapering outlet 2 from which the screw plug has been removed. The container 1 has seated thereon a protective cap 3 which is e.g. secured in a clamp fit to a shoulder of the container.

The protective cap 3 has substantially the form of a disk with a wave-like upper protective cap wall 4 which includes a concave indentation 5 approximately in the center and a respective convex bulge 6 at both sides. Centrally in the concave indentation 5, a hole 7 is formed that is positioned above the exit opening of the outlet 2 of the container.

Figure 2:
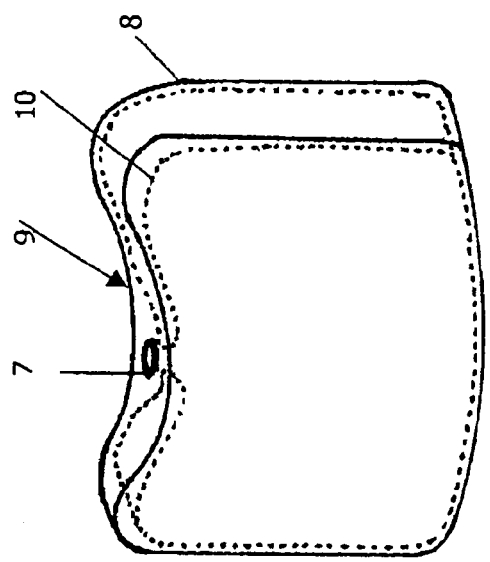
FIG. 2 is a prespective view of an embodiment of the container of the invention.

FIG. 2 shows a container 8 of the invention whose upper container wall 9 in the illustration has the same contour as the protective cap 3. Inside the outer container 8, a soft inner bag 10 is arranged that is connected in the area of the upper container wall 9 to the outer container and has an exit opening adjoining exit opening 7.

The container 11 shown in FIG. 3 is again equipped with a soft inner bag 12 whose exit opening communicates with the exit opening 13 of the container, which is again formed in the center in an indentation of the wave-like container wall 14. The inner bag 12 is positioned between two clamp jaws 15 that are movable by a motor 16 towards one another. This operation is started by exerting pressure on a push button 17. Batteries 18 are arranged for the supply of power to the motor 16. The container 11 may e.g. be opened by unfolding a side wall to replace the inner bag 12 or the batteries 18.

Figure 4B:
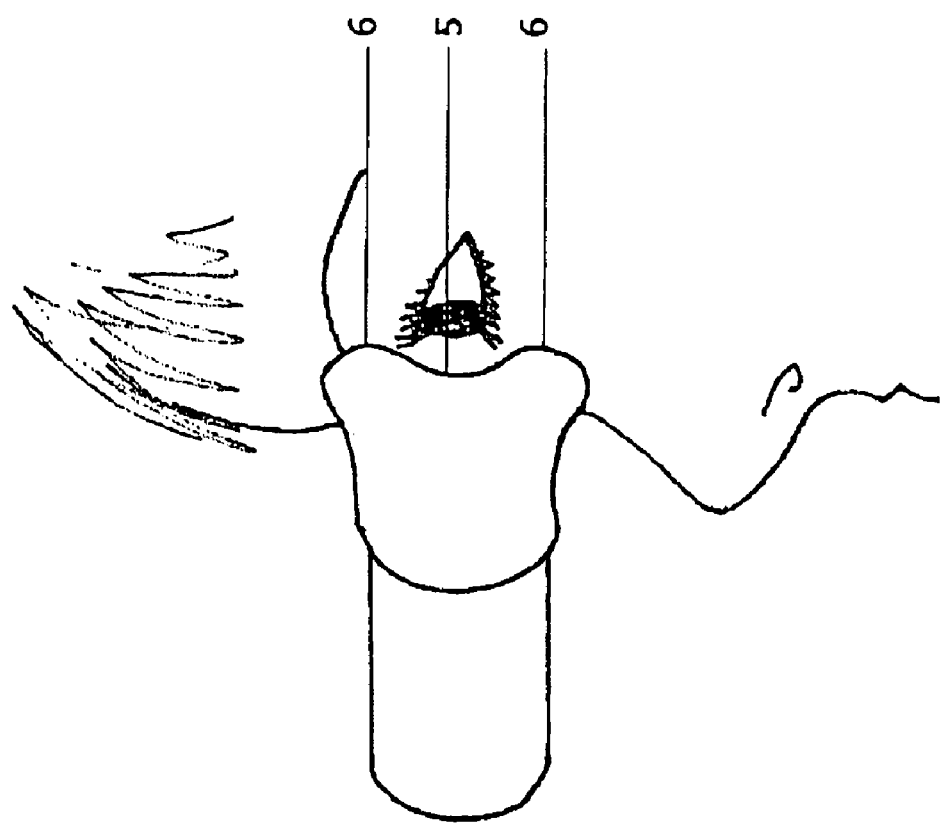
FIGS. 4A and 4B are two successive states during use of the container of the invention or the protective cap of the invention.
Figure 4A:
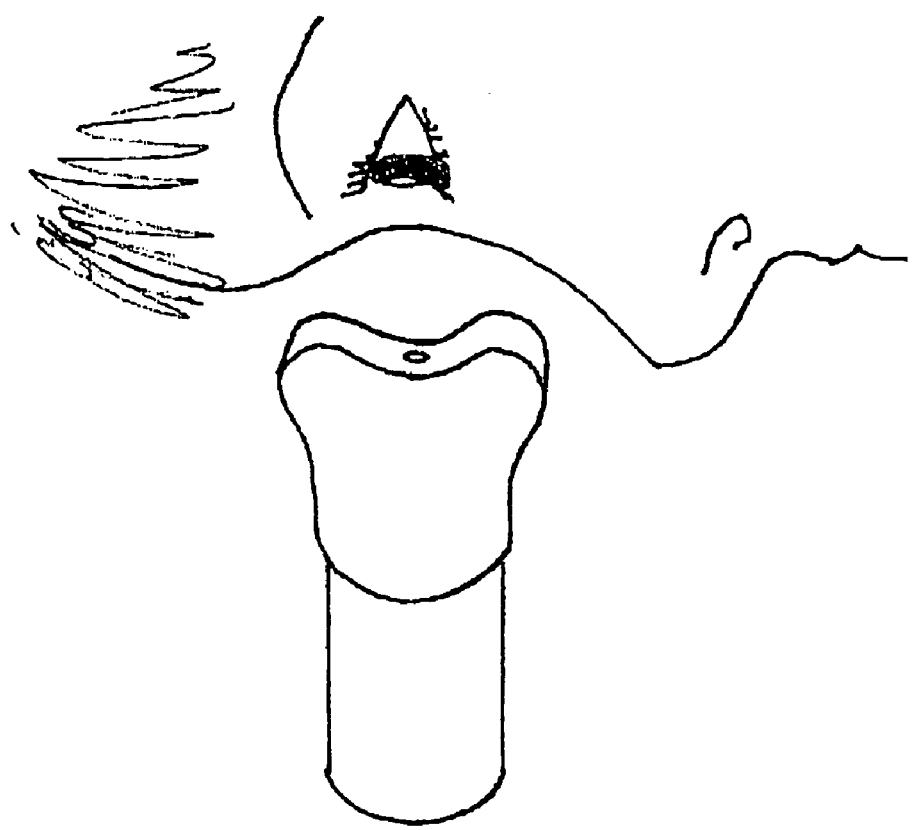

FIGS. 4A and 4B show that the protective cap 3 which is connected to an existing container, or the container 8 or 11 is moved towards the eye and is then placed with the two arcuate bulges 6 on the area of the eyebrow and cheekbones. In this position, the eye is spaced apart from the protective cap wall or container wall due to the indentation 5, so that an injury of the eye is safely excluded. The exit opening is exactly positioned above the eye by placing the protective cap or the container on the area of the eyebrow and cheekbones.

Figure 3:
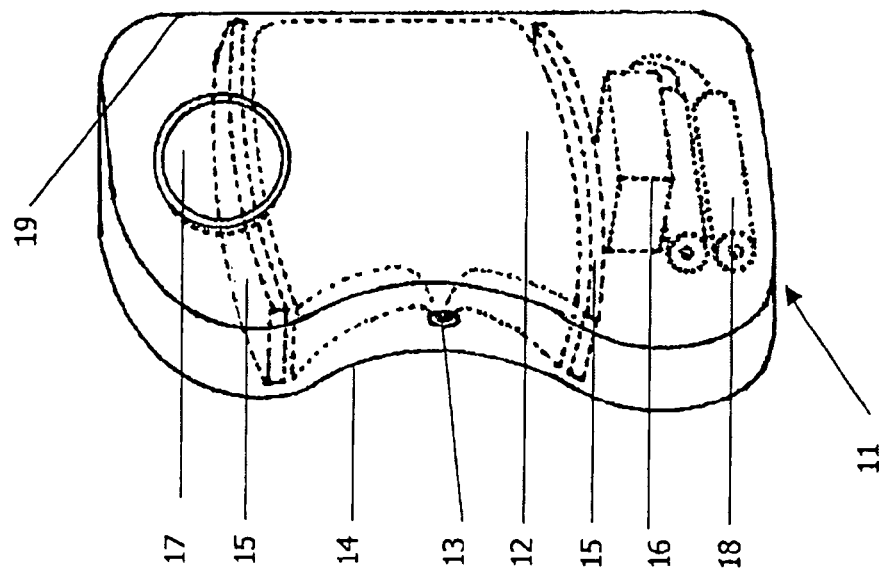
FIG. 3 is a prespective view of a second embodiment of the container of the invention.

For the administration of eye drops the container 11 shown in FIG. 3 may rest on the container wall 19 facing away from the exit opening 13 so that the exit opening 13 faces upwards. The eye drops are ejected upwards by motor power with an appropriate slight pressure.

The invention claimed is:

1. A container for medical ophthalmic preparations, comprising;
   an exit opening being formed in an indentation of the container wall;
   an outer container and a soft inner bag;
   said outer container has arranged therein a pressure generating means for the inner bag actuable by an electric motor; and
   said inner bag is arranged between clamp jaws which are movable towards one another by motor power.

2. The container according to claim 1, wherein said indentation has a concave arc shape and passes at both sides into a respective convex arcuate bulge.

* * * * *

UNITED STATES PATENT AND TRADEMARK OFFICE
CERTIFICATE OF CORRECTION

PATENT NO. : 7,296,710 B2 Page 1 of 1
APPLICATION NO. : 10/909510
DATED : November 20, 2007
INVENTOR(S) : Petschner It is certified that error appears in the above-identified patent and that said Letters Patent is hereby corrected as shown below:

On the Face:
On title page item [56]
Under Foreign Application Priority Data, add --August 2, 2003 (DE) 103 35 549.9--

Signed and Sealed this

Twentieth Day of May, 2008

JON W. DUDAS
*Director of the United States Patent and Trademark Office*